(12) United States Patent
Zemlok et al.

(10) Patent No.: US 9,364,222 B2
(45) Date of Patent: *Jun. 14, 2016

(54) POWERED SURGICAL STAPLING DEVICE PLATFORM

(71) Applicant: COVIDIEN LP, Mansfield, MA (US)

(72) Inventors: Michael Zemlok, Prospect, CT (US); David C. Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 533 days.

This patent is subject to a terminal disclaimer.

(21) Appl. No.: 13/889,580

(22) Filed: May 8, 2013

(65) Prior Publication Data

US 2013/0284790 A1 Oct. 31, 2013

Related U.S. Application Data

(60) Continuation of application No. 12/869,193, filed on Aug. 26, 2010, now Pat. No. 8,459,521, which is a division of application No. 11/799,766, filed on May 1, 2007, now Pat. No. 7,823,760.

(51) Int. Cl.
*A61B 17/068* (2006.01)
*A61B 17/072* (2006.01)
*A61B 17/00* (2006.01)
*A61B 17/29* (2006.01)

(52) U.S. Cl.
CPC ......... *A61B 17/068* (2013.01); *A61B 17/07207* (2013.01); *A61B 2017/00084* (2013.01);
(Continued)

(58) Field of Classification Search
CPC .................. A61B 17/068; A61B 2017/00199; A61B 2017/00734; A61B 2017/00398

USPC ........................................... 227/175.1, 179.1
See application file for complete search history.

(56) References Cited

U.S. PATENT DOCUMENTS 37,165 A 12/1862 Gary
3,079,606 A 3/1963 Bobrov et al.
(Continued)

FOREIGN PATENT DOCUMENTS

EP 0 537 570 B1 4/1993
EP 0634144 A1 1/1995
(Continued)

OTHER PUBLICATIONS

Extended European Search Report for EP 08 25 1568 dated Jun. 11, 2015.
European Search Report dated Jul. 28, 2011 for EP 11 15 2266.
U.S. Appl. No. 12/796,194, filed Jun. 8, 2010.
U.S. Appl. No. 12/959,421, filed Dec. 3, 2010.
(Continued)

*Primary Examiner* — Michelle Lopez

(57) ABSTRACT

The present disclosure provides for a surgical instrument which includes a housing and an endoscopic portion extending distally from the housing and defining a first longitudinal axis. The surgical instrument also includes an end effector disposed adjacent a distal portion of the endoscopic portion. The end effector includes an anvil assembly and a cartridge assembly. The anvil assembly is pivotally coupled to the cartridge assembly to be movable from a first actuation position to at least one other second actuation position. The surgical instrument further includes a firing rod having a shaft defining a second longitudinal axis, the shaft having a cam member which is in mechanical cooperation with the anvil assembly and is configured to move the anvil assembly from the first actuation position to the at least one other second actuation position upon rotation of the firing rod about the second longitudinal axis.

20 Claims, 15 Drawing Sheets

(52) U.S. Cl.
CPC ............. *A61B2017/00199* (2013.01); *A61B 2017/00221* (2013.01); *A61B 2017/00398* (2013.01); *A61B 2017/00734* (2013.01); *A61B 2017/2905* (2013.01); *A61B 2017/2927* (2013.01)

(56) References Cited

U.S. PATENT DOCUMENTS

| | | |
|---|---|---|
| 3,209,754 A | 10/1965 | Brown |
| 3,273,562 A | 9/1966 | Brown |
| 3,490,675 A | 1/1970 | Green et al. |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,473,077 A | 9/1984 | Noiles et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | DelMedico |
| 4,930,494 A | 6/1990 | Takehana et al. |
| 4,954,952 A | 9/1990 | Ubhayakar et al. |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,042,707 A | 8/1991 | Taheri |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,254,130 A | 10/1993 | Poncet et al. |
| 5,258,008 A | 11/1993 | Wilk |
| 5,271,381 A | 12/1993 | Ailinger et al. |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |

(56) References Cited

U.S. PATENT DOCUMENTS

| | | | |
|---|---|---|---|
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Nenetti et al. |
| 5,735,848 A | 4/1998 | Yates et al. |
| 5,738,474 A | 4/1998 | Blewett |
| 5,755,726 A | 5/1998 | Pratt |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,814,038 A * | 9/1998 | Jensen ............... A61B 19/2203 403/316 |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,916,146 A | 6/1999 | Allotta et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Laby et al. |
| 6,716,233 B1 | 4/2004 | Whitman |
| 6,736,085 B1 | 5/2004 | Esnouf |
| 6,743,239 B1 | 6/2004 | Kuehn et al. |
| 6,792,390 B1 | 9/2004 | Burnside et al. |
| 6,793,652 B1 | 9/2004 | Whitman et al. |

(56) References Cited

U.S. PATENT DOCUMENTS

| | | |
|---|---|---|
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,678,117 B2 | 3/2010 | Hinman et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,815,090 B2 | 10/2010 | Marczyk |
| 7,823,760 B2 | 11/2010 | Zemlok et al. |
| 7,845,534 B2 | 12/2010 | Viola et al. |
| 7,950,560 B2 * | 5/2011 | Zemlok ............... A61B 17/068 227/175.1 |
| 8,459,521 B2 * | 6/2013 | Zemlok ............ A61B 17/07207 227/175.1 |
| 2002/0103489 A1 | 8/2002 | Ku |
| 2002/0111641 A1 | 8/2002 | Peterson et al. |
| 2002/0165541 A1 | 11/2002 | Whitman |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0145674 A1 | 7/2005 | Sonnenschein et al. |
| 2005/0177176 A1 | 8/2005 | Gerbi et al. |
| 2005/0187576 A1 | 8/2005 | Whitman et al. |
| 2005/0192609 A1 | 9/2005 | Whitman et al. |
| 2005/0247753 A1 | 11/2005 | Kelly et al. |
| 2005/0273085 A1 | 12/2005 | Hinman et al. |
| 2006/0000867 A1 | 1/2006 | Shelton, IV et al. |
| 2007/0023477 A1 | 2/2007 | Whitman et al. |
| 2007/0029363 A1 | 2/2007 | Popov |
| 2007/0039995 A1 | 2/2007 | Schwemberger et al. |
| 2007/0084897 A1 | 4/2007 | Shelton, IV et al. |
| 2007/0102472 A1 | 5/2007 | Shelton, IV |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV |
| 2007/0175955 A1 | 8/2007 | Shelton, IV et al. |
| 2007/0219563 A1 | 9/2007 | Voegele |
| 2007/0265640 A1 | 11/2007 | Kortenbach et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0245842 A1 | 10/2008 | Marczyk |
| 2008/0251568 A1 | 10/2008 | Zemlok et al. |
| 2008/0255413 A1 | 10/2008 | Zemlok et al. |
| 2008/0255418 A1 | 10/2008 | Zemlok et al. |
| 2008/0255607 A1 | 10/2008 | Zemlok |
| 2008/0281353 A1 | 11/2008 | Aranyi et al. |
| 2008/0314959 A1 | 12/2008 | Viola et al. |
| 2009/0032568 A1 | 2/2009 | Viola et al. |
| 2009/0090201 A1 | 4/2009 | Viola |
| 2009/0090763 A1 | 4/2009 | Zemlok et al. |
| 2009/0108048 A1 | 4/2009 | Zemlok et al. |
| 2010/0001036 A1 | 1/2010 | Marczyk et al. |
| 2010/0012702 A1 | 1/2010 | Marczyk |
| 2010/0089972 A1 | 4/2010 | Marczyk |
| 2010/0163596 A1 | 7/2010 | Marczyk |
| 2010/0200636 A1 | 8/2010 | Zemlok et al. |
| 2010/0252610 A1 | 10/2010 | Viola |
| 2010/0312257 A1 | 12/2010 | Aranyi |
| 2010/0320254 A1 | 12/2010 | Zemlok et al. |

FOREIGN PATENT DOCUMENTS

| | | |
|---|---|---|
| EP | 0 647 431 A2 | 4/1995 |
| EP | 0705571 A1 | 4/1996 |
| EP | 0 738 501 A1 | 10/1996 |
| EP | 0 770 354 A1 | 5/1997 |

(56) References Cited

FOREIGN PATENT DOCUMENTS

| EP | 1 070 487 A2 | 1/2001 |
|---|---|---|
| EP | 1 769 754 | 4/2007 |
| EP | 1 813 203 | 8/2007 |
| FR | 2 849 589 | 7/2004 |
| WO | WO 97/29694 | 8/1997 |
| WO | WO 97/40760 | 11/1997 |
| WO | WO 98/37825 | 9/1998 |
| WO | WO 99/52489 | 10/1999 |
| WO | WO 02/34140 | 5/2002 |
| WO | WO 03/026511 | 4/2003 |
| WO | WO 03/030743 | 4/2003 |
| WO | WO 2004/032760 | 4/2004 |
| WO | WO 2007/030753 | 3/2007 |
| WO | WO 2007/118179 | 10/2007 |

OTHER PUBLICATIONS

U.S. Appl. No. 12/965,013, filed Dec. 10, 2010.
Detemple, P., "Microtechnology in Modern Health Care", *Med Device Technol.* 9(9):18-25 (1998).
European Search Report EP 06026840 dated May 10, 2007.
European Search Report EP 08251357.3 dated Sep. 29, 2009.
European Search Report EP 08252703.7 dated Oct. 31, 2008.
European Search Report EP 08253184.9 dated Feb. 27, 2009.
International Search Report PCT/US06/21524 dated May 28, 2008.
U.S. Appl. No. 13/715,364, filed Dec. 14, 2012, Aranyi et al.
Patent Examination Report No. 1 for Australian Patent Appln. No. AU 2014-200667 dated Mar. 5, 2015.

\* cited by examiner

POWERED SURGICAL STAPLING DEVICE PLATFORM

CROSS REFERENCE TO RELATED APPLICATIONS

The present application is a Continuation Application of U.S. patent application Ser. No. 12/869,193, filed Aug. 26, 2010, which is Divisional Application of and claims the benefit of and priority to U.S. patent application Ser. No. 11/799,766, filed May 1, 2007, now U.S. Pat. No. 7,823,760, which is expressly incorporated herein by reference in its entirety.

BACKGROUND

1. Technical Field

The present disclosure relates to surgical instruments for fastening body tissue and, more particularly, to a powered surgical instrument having a firing rod configured to be movable and rotatable to affect rotation, articulation and actuation of portions of the instrument.

2. Background of Related Art

Surgical devices wherein tissue is grasped or clamped between opposing jaw structure and then joined by surgical fasteners are well known in the art. In some instruments, a knife is provided to cut the tissue which has been joined by the fasteners. The fasteners are typically in the form of surgical staples but two-part polymeric fasteners can also be utilized.

Instruments for this purpose may include two elongated members which are respectively used to capture or clamp tissue. Typically, one of the members carries a staple cartridge that houses a plurality of staples arranged in at least two lateral rows while the other member has an anvil that defines a surface for forming the staple legs as the staples are driven from the staple cartridge. Several instruments include clamps, handles and/or knobs to affect actuation along with rotation and articulation of an end effector. Generally, the stapling operation is effected by cam bars that travel longitudinally through the staple cartridge, with the cam bars acting upon staple pushers to sequentially eject the staples from the staple cartridge. Such stapling devices can be used in open as well as endoscopic and/or laparoscopic surgical procedures.

It would be extremely beneficial to provide a powered surgical device for use during surgical procedures that can utilize a new and improved mechanism for articulating and/or actuating the tool tip to automate the stapling process.

SUMMARY

According to one aspect of the present disclosure, a surgical instrument is provided. The surgical instrument includes a housing and an endoscopic portion extending distally from the housing and defining a first longitudinal axis. The surgical instrument also includes an end effector disposed adjacent a distal portion of the endoscopic portion. The end effector may include an anvil assembly and a cartridge assembly. The anvil assembly is pivotally coupled to the cartridge assembly to be movable from a first actuation position to at least one other second actuation position. The surgical instrument further includes a firing rod having a shaft defining a second longitudinal axis, the shaft having a cam member which is in mechanical cooperation with the anvil assembly and is configured to move the anvil assembly from the first actuation position to the at least one other second actuation position upon rotation of the firing rod about the second longitudinal axis.

According to another aspect of the present disclosure a surgical instrument is provided with a housing and an endoscopic portion extending distally from the housing and defining a first longitudinal axis. The surgical instrument also includes an end effector disposed adjacent a distal portion of the endoscopic portion. The end effector includes a first jaw member and a second jaw member, the second jaw member is pivotally coupled to the first jaw member to be movable from a first actuation position to at least one other second actuation position. The surgical instrument further includes a firing rod including a shaft defining a second longitudinal axis. The shaft has a cam member which is in mechanical cooperation with the second jaw member and is configured to move the second jaw member from the first actuation position to the at least one other second actuation position upon rotation of the firing rod about the second longitudinal axis.

According to a further embodiment of the present disclosure, a tool assembly is provided. The tool assembly includes an end effector disposed adjacent a distal endoscopic portion. The end effector includes an anvil assembly and a cartridge assembly. The anvil assembly is pivotally coupled to the cartridge assembly to be movable from a first actuation position to at least one other second actuation position. The tool assembly also includes a firing rod including a shaft defining a second longitudinal axis. The shaft has a cam member which is in mechanical cooperation with the anvil assembly and is configured to move the anvil assembly from the first actuation position to the at least one other second actuation position upon rotation of the firing rod about the second longitudinal axis.

According to another aspect of the present disclosure, a surgical instrument is disclosed, which includes a housing, an endoscopic portion extending distally from the housing and an intermediate shaft having a proximal end configured for connection to a distal end of the endoscopic portion, the intermediate shaft being flexible. The instrument also includes a loading unit having an end effector for performing a surgical function. The loading unit includes a proximal portion configured for connection to a distal end of the intermediate shaft.

According to a further aspect of the present disclosure, a surgical instrument including a housing and an endoscopic portion extending distally from the housing is disclosed. The housing includes at least a first angled tube and a second angle tube, the first angled tube and second angled tube being rotatably movable with respect to one another between a plurality of positions including a first position defining a substantially straight shaft and a second, fully articulated position and an end effector disposed adjacent a distal portion of the endoscopic portion.

DESCRIPTION OF THE DRAWINGS

An embodiment of the presently disclosed powered surgical instrument is disclosed herein with reference to the drawings, wherein.

DETAILED DESCRIPTION OF EMBODIMENTS

Figure 1:
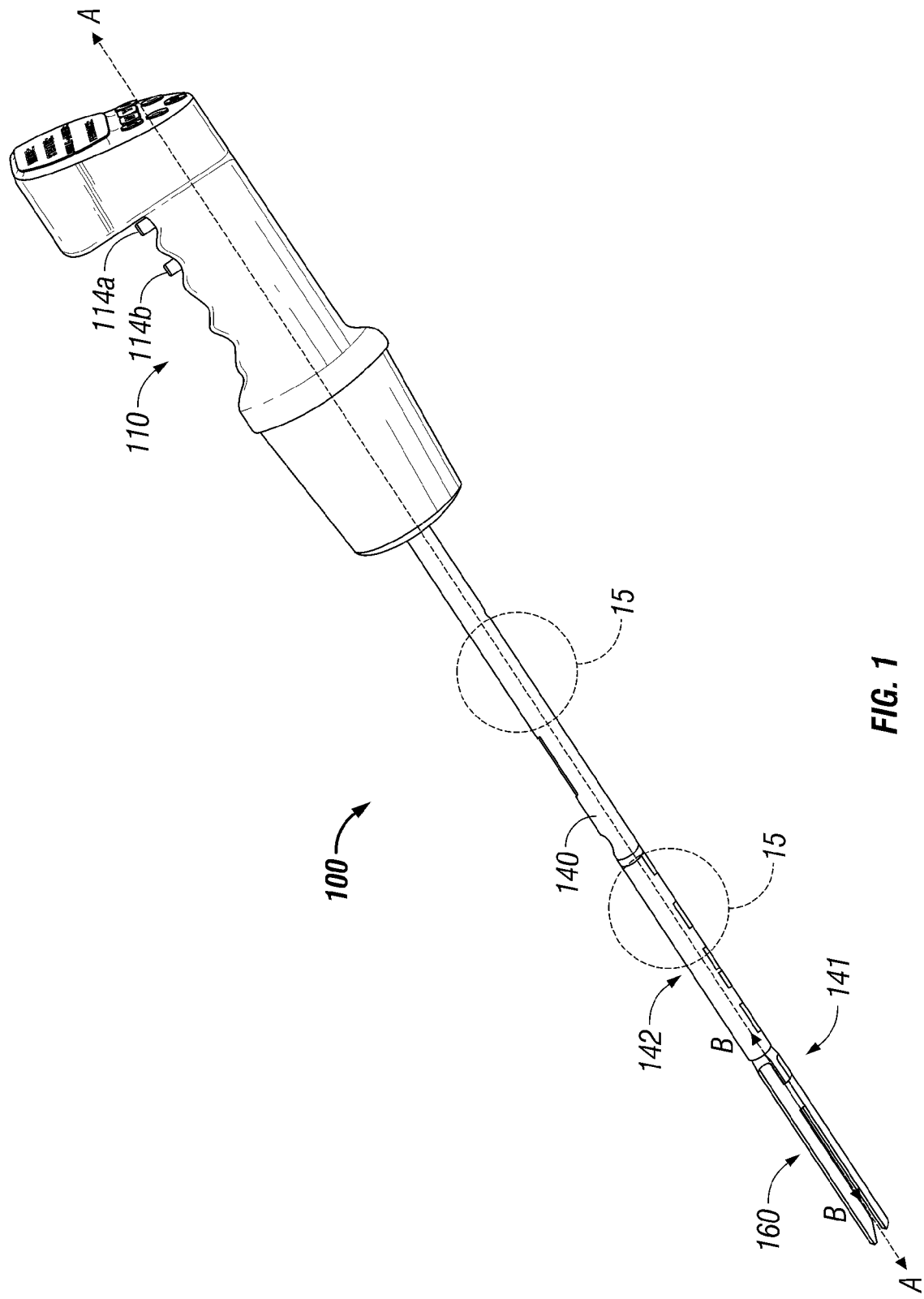
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 100. Referring initially to FIG. 1, powered surgical instrument 100 includes a housing 110, an endoscopic portion 140 defining a longitudinal axis A-A extending therethrough, and an end effector 160, defining a longitudinal axis B-B (illustrated substantially aligned with axis A-A in FIG. 1) extending therethrough. Endoscopic portion 140 extends distally from housing 110 and end effector 160 is disposed adjacent a distal portion 142 of endoscopic portion 140.

It is envisioned that end effector 160 is reusable and is configured to accept a staple cartridge and/or is part of a disposable loading unit. Further details of a disposable loading unit are described in detail in commonly-owned U.S. Pat. No. 6,241,139 to Miliman, the entire contents of which are hereby incorporated by reference herein.

The end effector 160 is coupled to the endoscopic portion 140 via a mounting assembly 141. The end effector 160 may be any end effector used in linear stapling devices, such as ENDO GIA™, GIA™, TA™, ENDO TA™, EEA™ staplers sold by U.S. Surgical Corp, of Norwalk, Conn. Such end effectors may be coupled to endoscopic portion 140 of powered surgical instrument 100. Mounting assembly 141 is pivotally secured to the distal portion 142 and is fixedly secured to a proximal end of tool assembly 160. This allows for pivotal movement of mounting assembly 141 about an axis perpendicular to the longitudinal axis A-A. Pivotal movement occurs between a non-articulated position in which the longitudinal axis of tool assembly 160 is aligned with the longitudinal axis A-A and an articulated position in which the longitudinal axis B-B of the tool assembly 160 is disposed at an angle to the longitudinal axis A-A of endoscopic portion 140.

Figure 2:
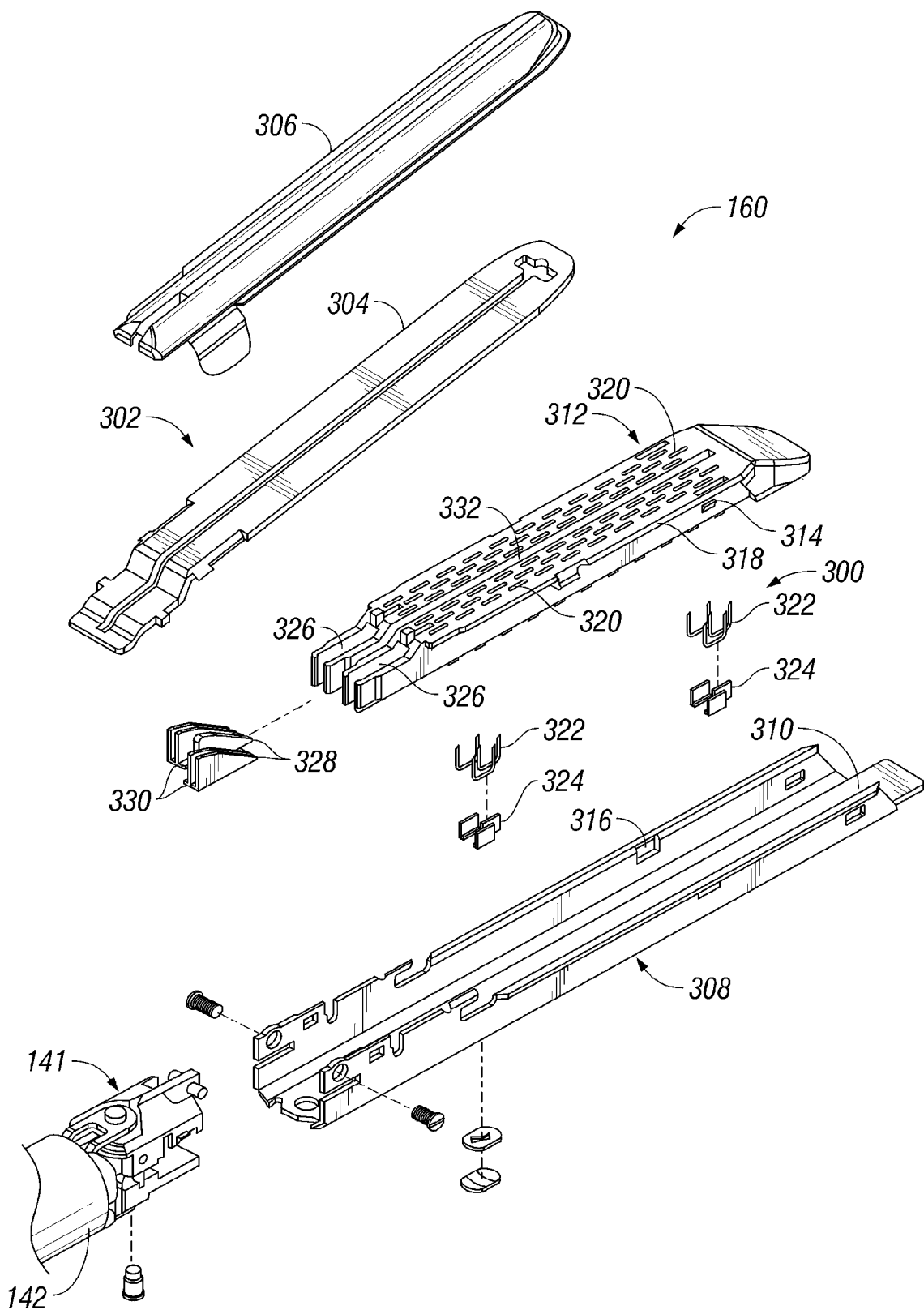
FIG. 2 is an exploded view of the staple cartridge and anvil or business head of the surgical instrument shown in FIG. 1.
Figure 3:
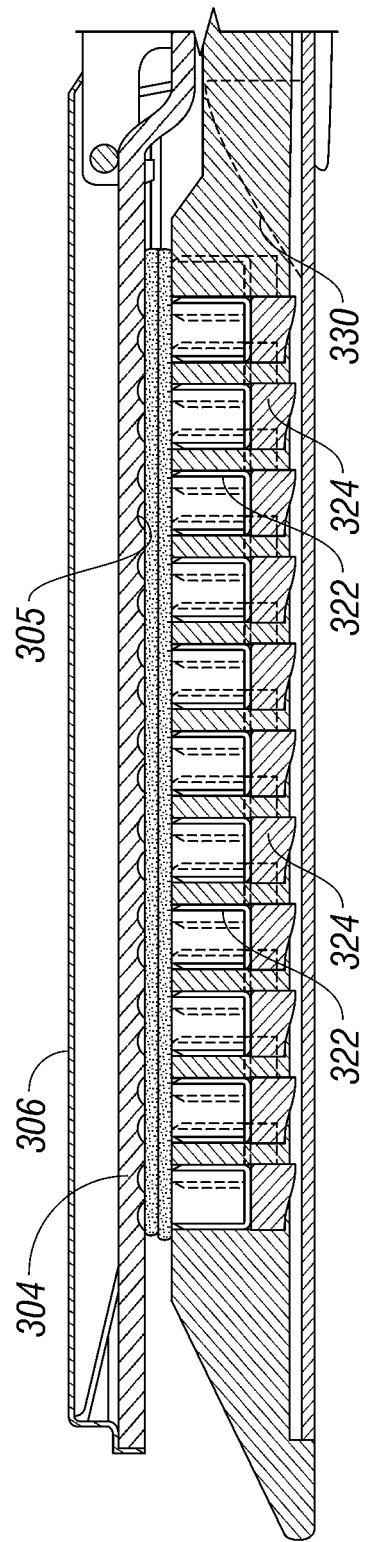
FIG. 3 is a side cross-sectional view of the staple cartridge and anvil or business head of the surgical instrument shown in FIG. 1.

Referring to FIGS. 2 and 3, tool assembly 160 includes a cartridge assembly 300 (e.g., first jaw of the tool assembly) and an anvil assembly 302 (e.g., second of the tool assembly). Anvil assembly 302 includes an anvil portion 304 having a plurality of staple deforming concavities 305 (FIG. 3) and a cover plate 306 secured to a top surface of anvil portion 304. Cartridge assembly 300 includes carrier 308 which defines an elongated support channel 310 which is dimensioned and configured to receive staple cartridge 312. Corresponding tabs 314 and slots 316 formed along staple cartridge 312 and elongated support channel 310, respectively, function to retain staple cartridge 312 at a fixed location within support channel 310. A pair of support struts 318 formed on staple cartridge 312 is positioned to rest on side walls of carrier 308 to further stabilize staple cartridge 312 within support channel 310.

Staple cartridge 312 includes retention slots 320 for receiving a plurality of staples or fasteners 322 and pushers 324. A plurality of laterally spaced apart longitudinal slots 326 extends through staple cartridge 312 to accommodate upstanding cam wedges 328 of an actuation sled 330. A central longitudinal slot 332 extends along substantially the length of staple cartridge 312 to facilitate passage of a knife blade (not explicitly shown).

Figure 4A:
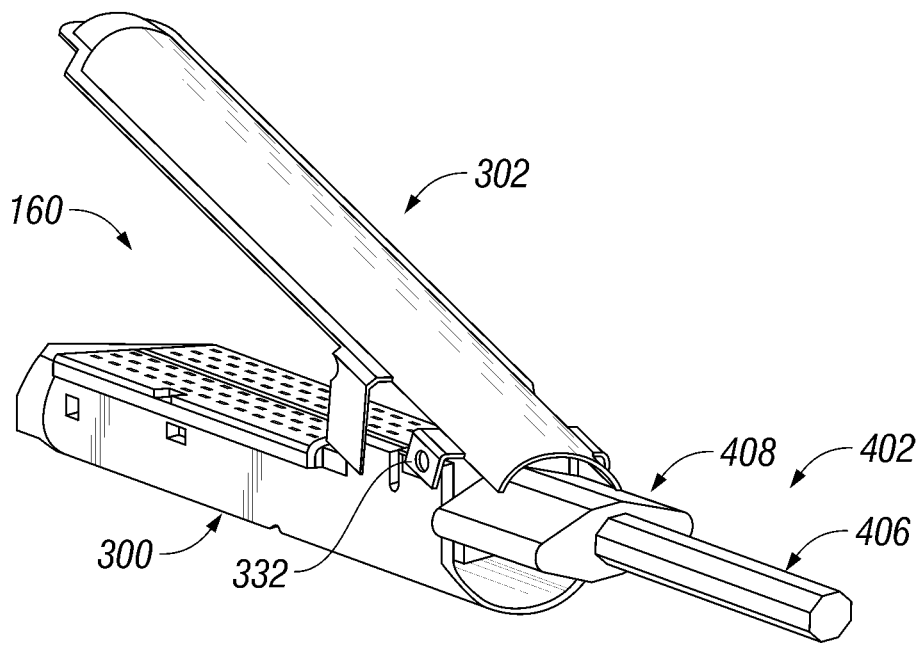
FIGS. 4A-B are perspective views of a shaped firing rod and cammed clamping of the stapler anvil in the open and closed positions.
Figure 4B:
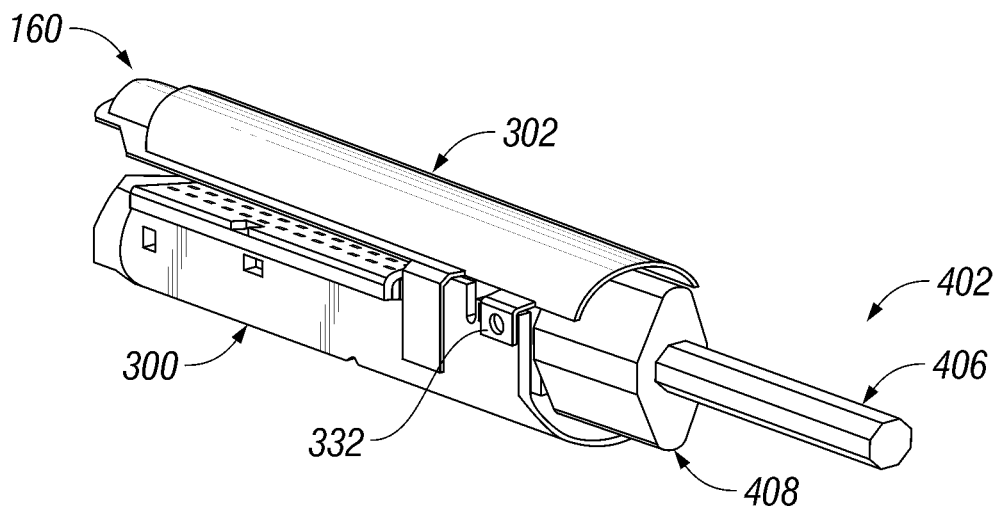
Figure 5:
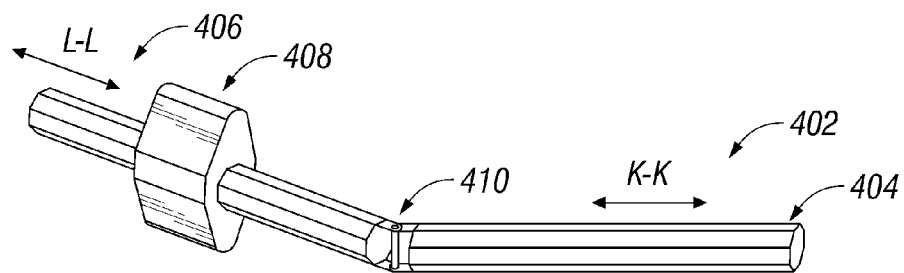
FIG. 5 is a perspective view of the cam and the shaped firing rod of the surgical instrument of FIG. 1.

FIGS. 4A-B and 5 show a firing rod 402 for articulation and actuation of the tool assembly 160. The firing rod 402 includes a proximal shaft 404 which extends the length of the endoscopic portion 140 and the distal portion 142 and a distal shaft 406 which is disposed within the tool assembly 160. The proximal shaft 404 and the distal shaft 406 are pivotally linked via a pivot member 410 which passes through bores (not explicitly shown) within the distal end of the proximal shaft 404 and the proximal end of the distal shaft 406. Pivotal movement occurs between a non-articulated position in which the longitudinal axis of distal shaft 406 is aligned with the longitudinal axis K-K and an articulated position in which the longitudinal axis L-L of the tool distal shaft 406 is disposed at an angle to the longitudinal axis K-K of proximal shaft 404. The firing rod 402 may be formed from a rigid and/or flexible material. Forming the firing rod 402 from a flexible material obviates the need for pivot member 410 as the proximal shaft 404 can pivot with respect to the distal shaft 406 by nature of the flexibility of the material. It is envisioned that other pivoting mechanisms may be used, such as plastic or rubber bands interconnecting the proximal and distal portions 404 and 406.

The proximal shaft 404 and the distal shaft 406 of the firing rod 402 incorporate a plurality of surface features or shapes along the length thereof. In embodiments, the firing rod 402 has a generally cylindrical structure with a non-circular cross-section (e.g., hexagonal, octagonal, star-shaped, oval, etc.) It is also envisioned the firing rod 402 may include one or more curved shapes (e.g., helix, screw, etc.) These structures allow for gripping of the firing rod 402 and rotation thereof to actuate the tool assembly 160.

The firing rod 402 is disposed within a passage (not explicitly shown) of the endoscopic portion 140 and the distal portion 142, the passage has the same cross-sectional profile as the firing rod 402 such that the firing rod 402 is in mechanical cooperation with the passage but can simultaneously freely slide therein. This is especially useful if the firing rod 402 is formed from a flexible material since this prevents deformation of the firing rod 402 within the passage.

The firing rod 402 is configured for opening and closing of the anvil assembly 302 as well as pushing actuation sled 330 through longitudinal slots 326 of staple cartridge 312 to advance cam wedges 328 into sequential contact with pushers 324 to staple tissue. The firing rod 402 is configured to be selectively moved between a plurality of positions. In certain embodiments, the firing rod 402 is moved between at least two positions. The first position, illustrated in FIG. 4A, enables opening and closing of the anvil assembly 302 via rotation of the firing rod 402 about longitudinal axis K-K; the second position, illustrated in FIG. 4B, enables advancement of pushers 324 to push fasteners 322 through tissue.

In FIG. 4A the firing rod 402 is shown in the first position. The distal shaft 406 of the firing rod 402 includes a cam member 408, which is shown as a dual cam, disposed thereon. In the first position, the cam member 408 is positioned in a plane perpendicular to the longitudinal axis L-L at the distal end of the anvil assembly 302. During operation, the firing rod 402 is rotated, which causes rotation of the cam member 408. As the cam member 408 is rotated, the proximal end of the anvil assembly 302 is pushed upwards by the perpendicular displacement of the cam member 408 thereby closing the anvil assembly 302 against the cartridge assembly 300 (FIG. 4B).

The anvil assembly 302 is pivotally coupled to the cartridge assembly via tabs 332 which extend downwards therefrom. The tabs 332 fit into corresponding slots (not explicitly shown) to provide a hinge point for the anvil assembly 332 to pivot thereabout. This allows the anvil assembly 302 to pivot with respect to the cartridge assembly 300. As the firing rod 408 is rotated further the anvil assembly 302 reverts to open position via one or more biasing members (e.g., springs) pushing upwards on the opposite side of the tabs 332.

Various types of cams may be used to open and close the anvil assembly 302, such as single cams, or multi-cams. Other cam shapes may also be utilized which have a less aggressive angle utilizing full 360° of rotation allowing the anvil assembly 302 to reach full displacement at a more gradual rate. Angle of rotation of the firing rod 402 varies with the type of cam being used, such as for the cam member 408, the firing rod 402 is rotated 90° in order to actuate the anvil assembly 302. In other words, the cam member 402 allows for maximum displacement of the anvil assembly 302 under 90°. It is also envisioned that the firing rod 402 may be rotated in either direction, clockwise or counterclockwise, to actuate the anvil assembly 302.

While in the first position the firing rod 402 is prevented from longitudinal movement in the distal direction by the proximal end of the cartridge assembly 300 and the cam member 408. The walls of the support channel 310 act as a stop member when the firing rod 402 is moved in the distal direction. Once the firing rod 402 is rotated into second position as shown in FIG. 4B, the firing rod 402 can be advanced distally to push the actuation sled 330 through the staple cartridge 312 since the firing rod 402 is no longer stopped by the distal end of the cartridge assembly. The firing rod 402 is movable through the cam member 408, the interface between an aperture through the cam member 408 and the firing rod 402 being shaped to allow a telescoping movement, but also shaped so that the cam member 408 and firing rod 402 rotate together. For example, the cam member 408 and firing rod 402 have a hexagonal shaped interface as shown in FIGS. 4A and 4B. Other shapes, such as helical, star shaped, splined, oval, slotted, and octagonal, can be used.

During operation of surgical stapler, the firing rod 402 abuts actuation sled 330 and pushes actuation sled 330 through longitudinal slots 326 of staple cartridge 312 to advance cam wedges 328 of sled 330 into sequential contact with pushers 324. Pushers 324 translate vertically along cam wedges 328 within fastener retention slots 320 and urge fasteners 322 from retention slots 320 into staple deforming cavities 304 (FIG. 4) of the anvil assembly 302.

Figure 6:
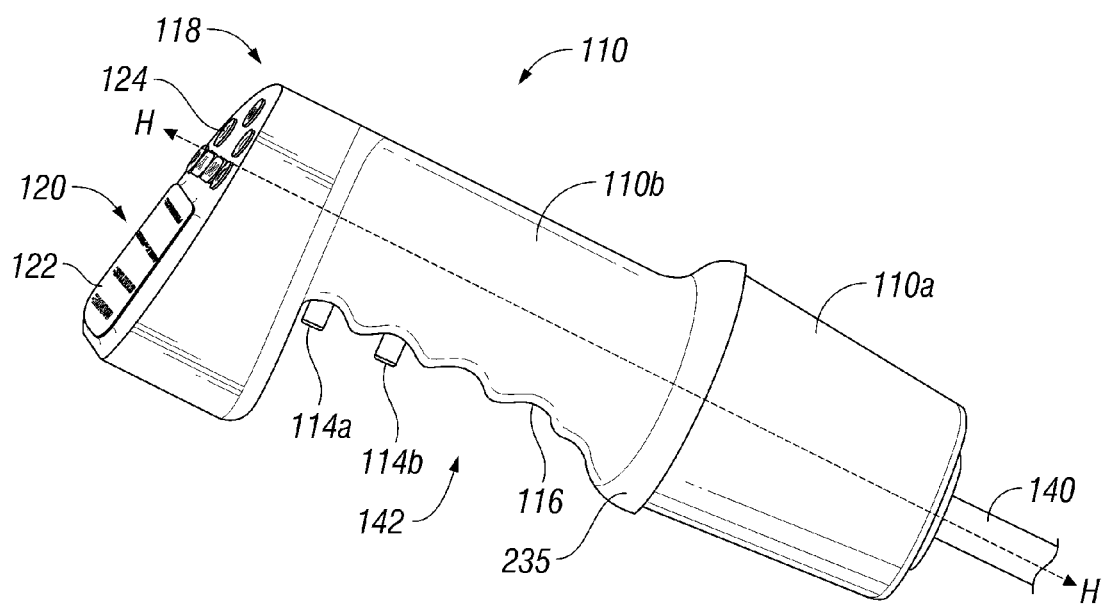
FIG. 6 is an enlarged perspective view of a handle of the powered surgical instrument of FIG. 1.
Figure 7:
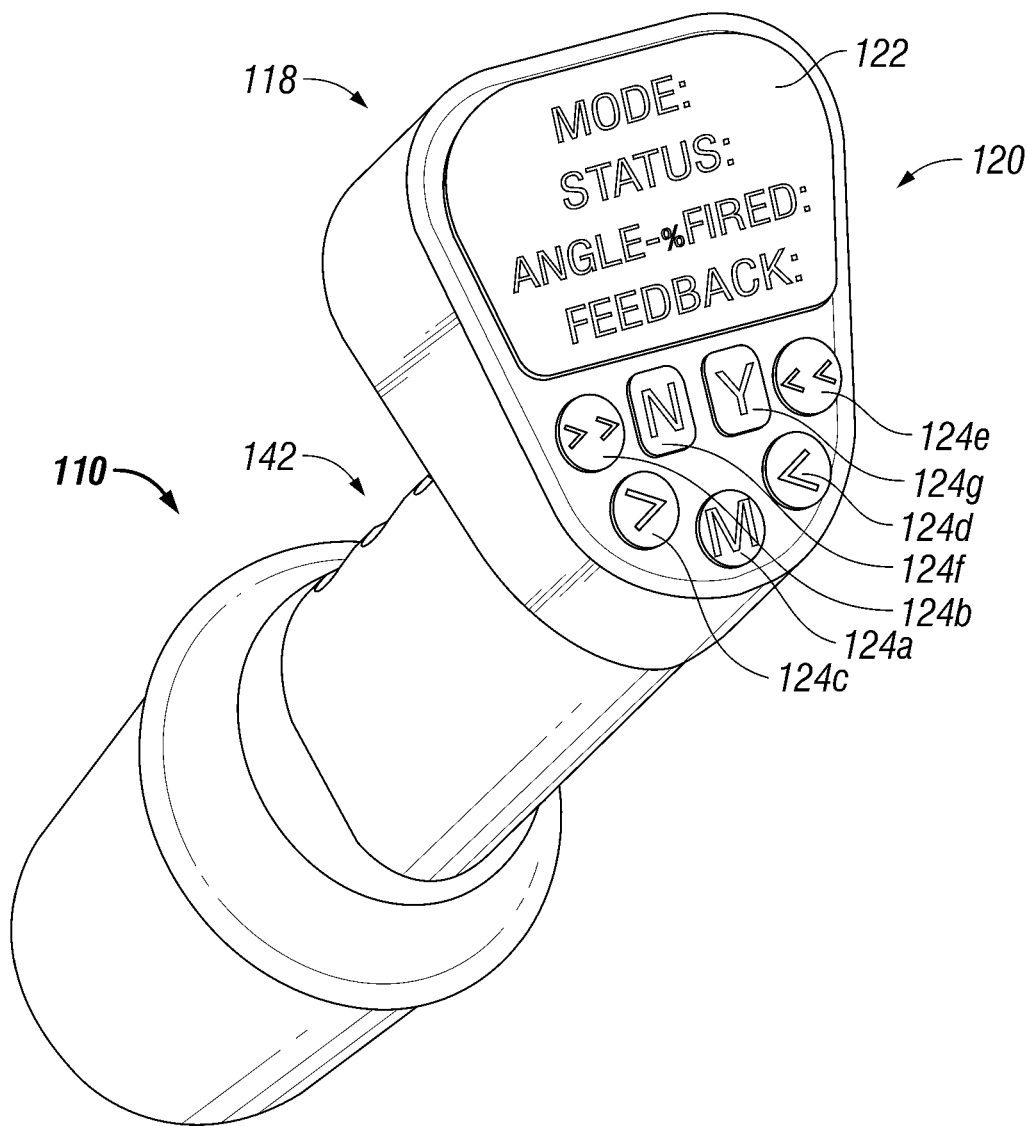
FIG. 7 is an enlarged perspective view of a user interface of the powered surgical instrument of FIG. 1.

With reference to FIGS. 6 and 7, an enlarged view of housing 110 is illustrated according to an embodiment of the present disclosure. In the illustrated embodiment, housing 110 includes a handle portion 110b having two buttons 114a and 114b. Handle portion 110b, which defines a handle axis H-H, is shown having indentations 116 that correspond to fingers of a user. Each button 114a and 114b is shown as being disposed on an indentation 116 to facilitate its depression by a user's finger.

A proximal area 118 of housing 110 includes a user interface 120. In the illustrated embodiment, user interface 120 includes a screen 122 and at least one switch 124 (seven switches 124a-124g are shown). Screen 122 displays readable information thereon, including status information of powered surgical instrument 100 in an embodiment.

FIG. 7 shows user interface 120 including screen 122 and seven switches 124a-124g. In the illustrated embodiment, user interface displays the "mode" (e.g., rotation, articulation or actuation), which may be communicated to user interface 120 via shift sensor 224, "status" (e.g., angle of articulation, speed of rotation, or type of actuation) and "feedback," such as whether staples have been fired. Switch 124a is shown having an "M," standing for mode, which may be used to position drive gear 200 via shift motor 220 for selecting between rotation, articulation, grasping, clamping and firing. It is also envisioned that switch 124a can be used to let a user input different tissue types, and various sizes and lengths of staple cartridges.

Switches 124b-124e are shown with arrows thereon and may be used for selecting the direction, speed and/or torque at which drive gear 200 is rotated by drive motor 210. It is also envisioned that at least one switch 124 can be used for selecting an emergency mode that overrides various settings. Further, switches 124f and 124g are illustrated having an "N" and a "Y" thereon. It is envisioned that switches 124f and 124g may be used for helping a user navigate user interface menus and select various setting of powered surgical instrument 100. The indicia on switches 124a-124g and their respective functions are not limited by what is shown in the accompanying figures, as deviations therefrom are contemplated and within the scope of the present disclosure. Additionally, and with reference to FIGS. 1 and 6, buttons 114a and 114b may be used for starting and/or stopping movement of drive motor 210 and/or shift motor 220 and the like.

FIGS. 8-14 illustrate various internal components of powered surgical instrument 100, including a drive gear 200, a drive motor 210 and a shift motor 220. Power is provided via a battery pack 401 (or fuel cell assembly). Other power-supplying means are also contemplated (e.g., electrical transformers coupled to conventional electrical power supplies).

Figure 8:
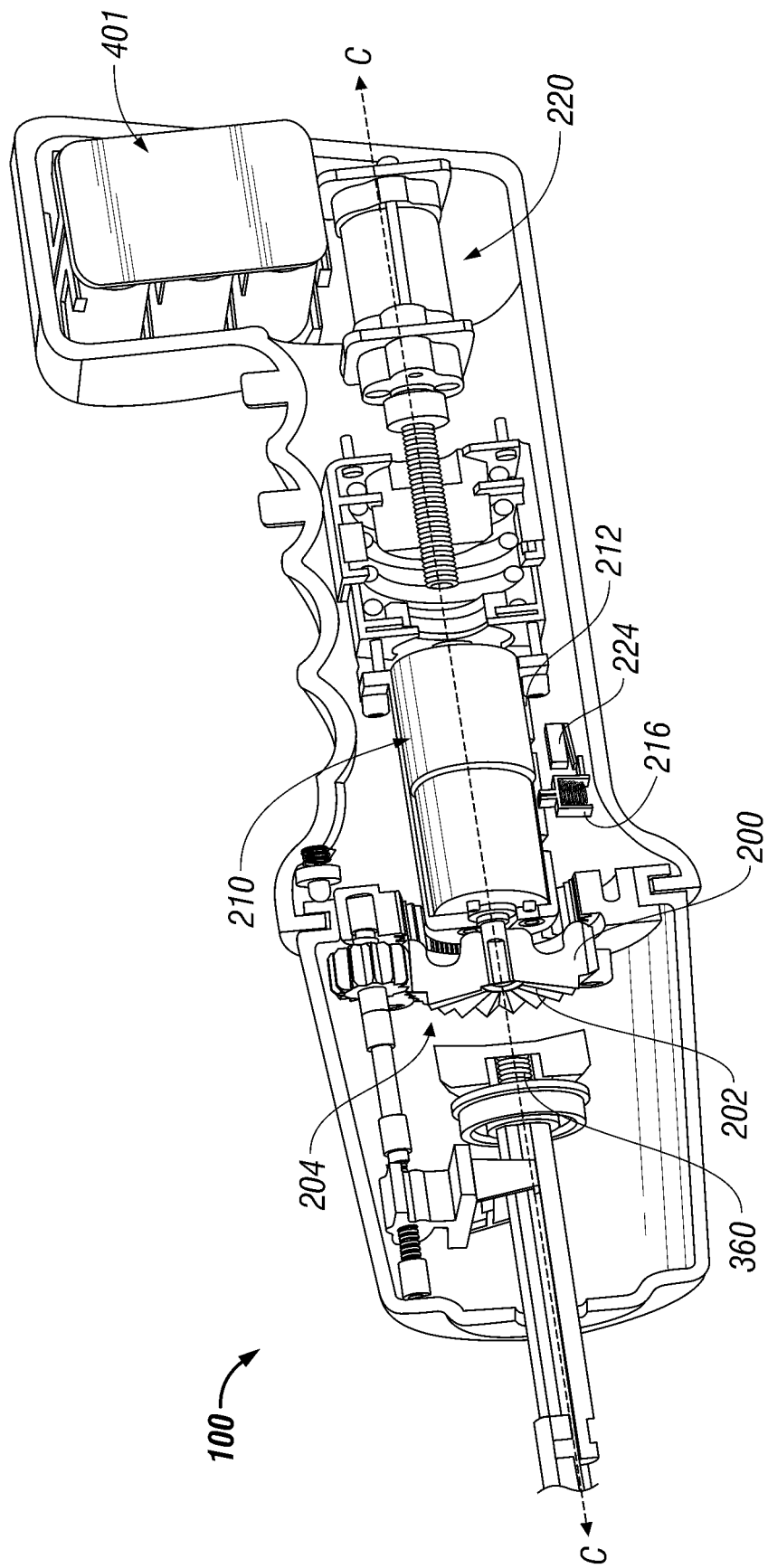
FIG. 8 is a perspective view of internal components of the powered surgical instrument of FIG. 1.

As shown in FIG. 8, the drive gear 200, the drive motor 210 and the battery pack 401 are disposed within the housing 110, specifically a proximal housing portion 110b. It is envisioned that these components may also be located within or closer to a distal housing portion 110a. The primary or a secondary motor, transmission, and/or the batteries may be disposed in the endoscopic portion 140.

Drive gear 200 is rotatable about a drive gear axis C-C extending therethrough (FIG. 8) and is selectively movable along drive gear axis C-C. Drive motor 210 is disposed in mechanical cooperation with drive gear 200 and is configured to rotate drive gear 200 about drive gear axis C-C. Shift motor 220 is disposed in mechanical cooperation via the drive motor 210 with drive gear 200 and is configured to translate drive gear 200 axially along drive gear axis C-C.

Shift motor 220 is configured to selectively move drive gear 200 between a plurality of positions. In embodiments, the drive gear 200 is moved between three positions. The first position, illustrated in FIGS. 9 and 10, enables rotation of end effector 160; the second position, illustrated in FIG. 11, enables articulation of end effector 160; and the third position, illustrated in FIGS. 13-14, enables actuation of powered surgical instrument 100.

Figure 9:
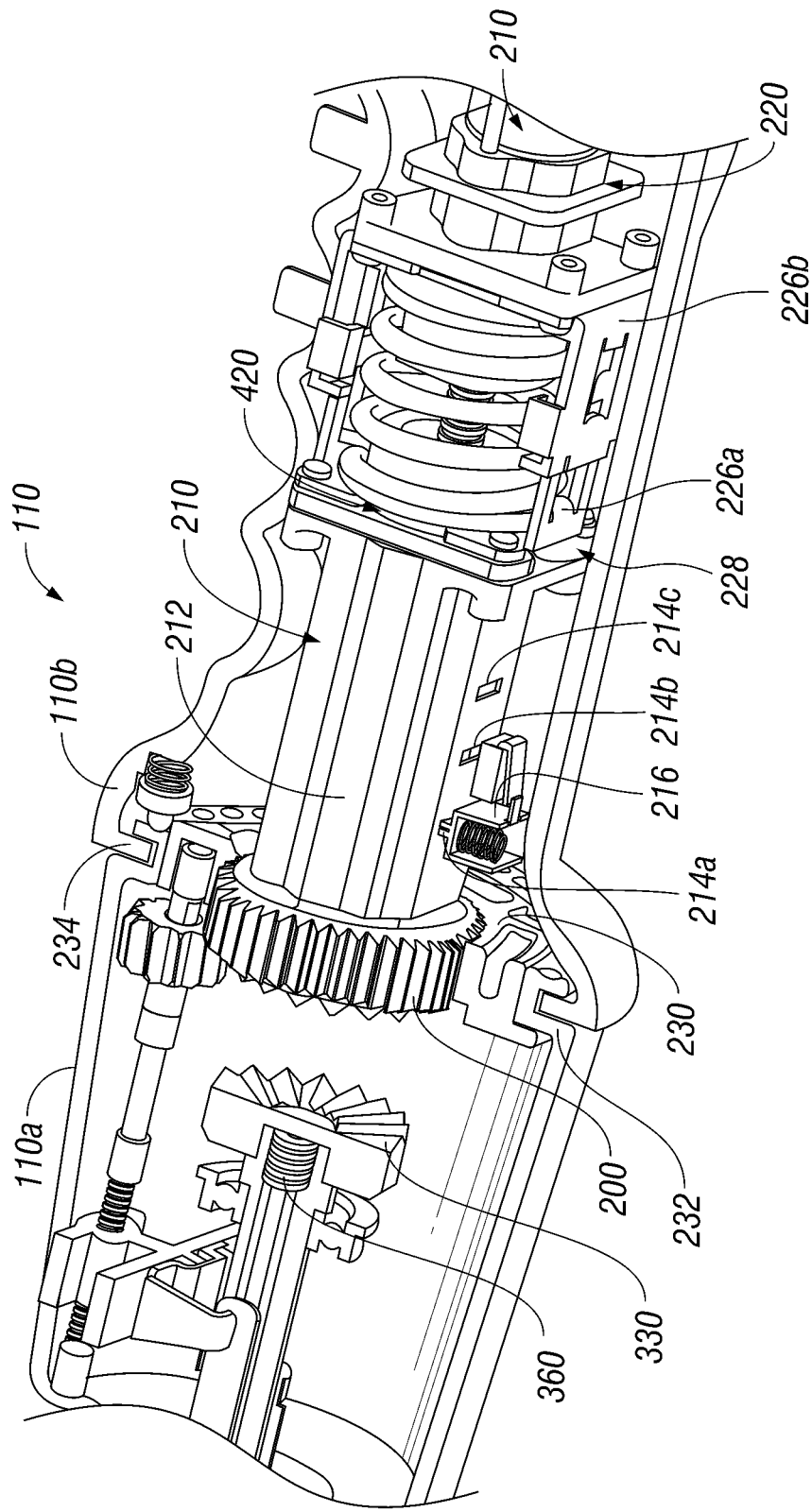
FIGS. 9 and 10 are perspective views of the internal components of the powered surgical instrument of FIG. 1 disposed in a first position, powered rotation.

In the embodiment illustrated in FIG. 9, shift motor 220 is shown including a two-part housing 226. Each part 226a and 226b of two-part housing 226 are slidably engaged with each other. It is envisioned that part 226a is rigidly secured to a drive motor casing 212, while part 226b is affixed to drive motor 210 and is translatable within housing 110. Additionally, a wiring slot 228 may be included to allow for wires (not explicitly shown) to pass from transducer 420 towards user interface 120, for example.

Figure 10:
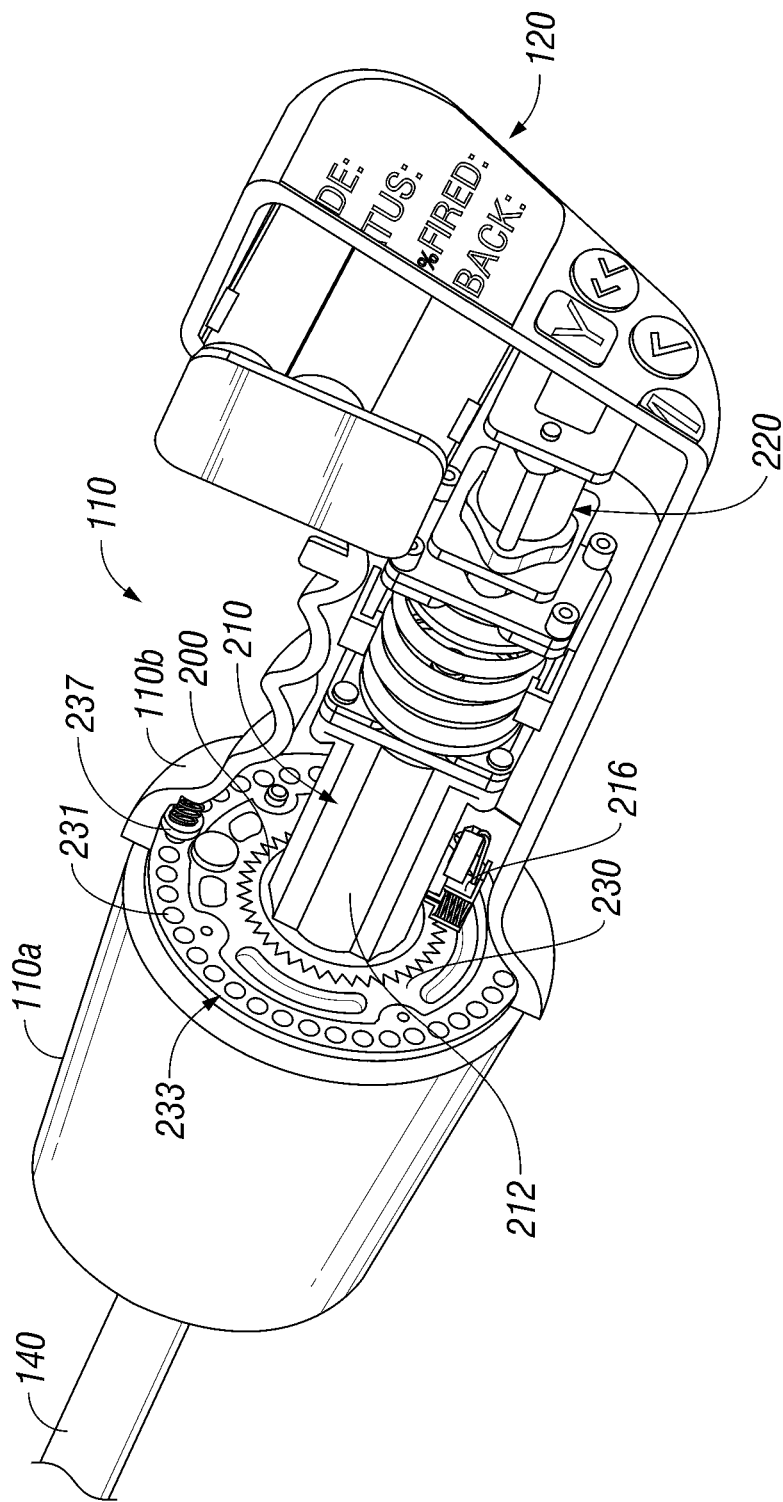
Figure 11:
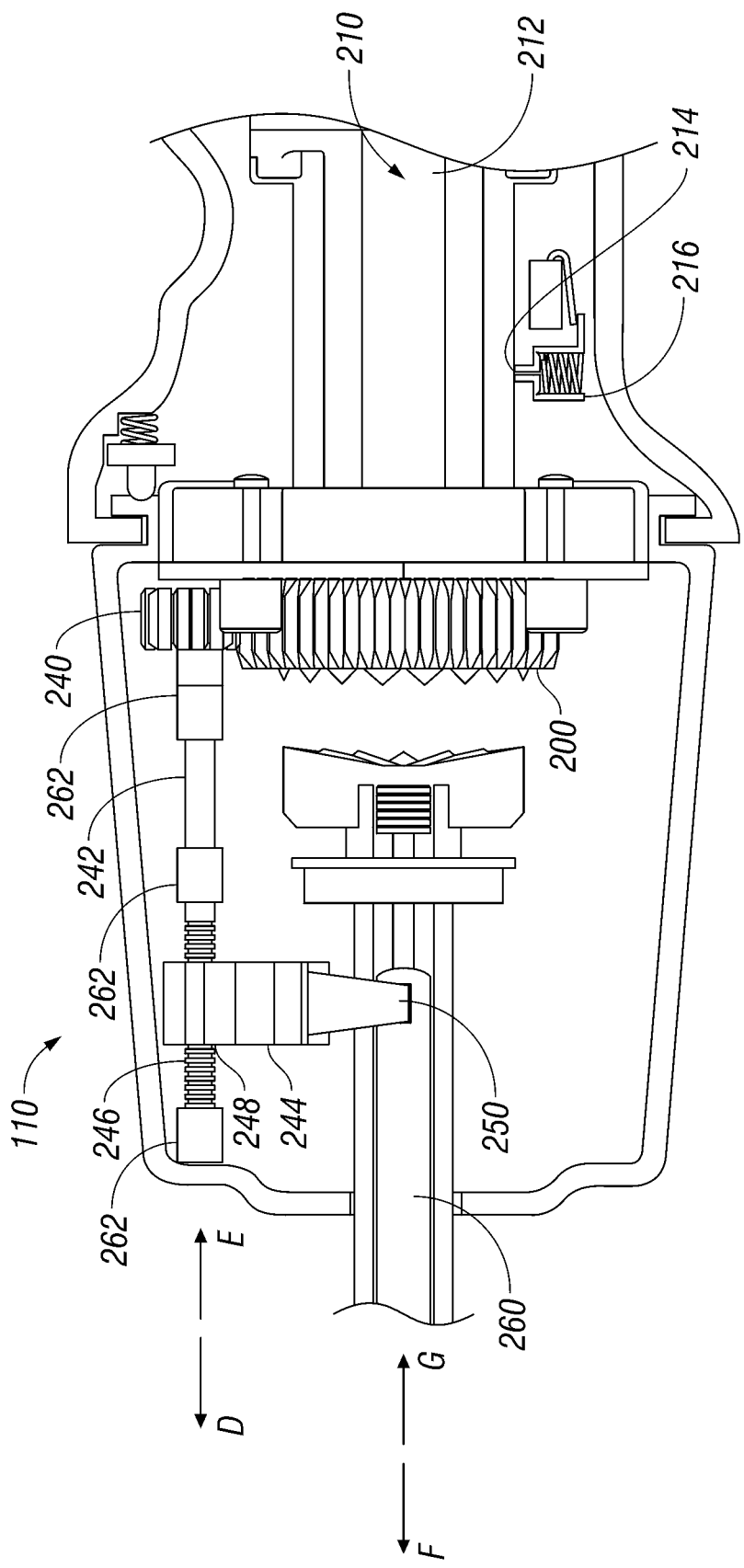
FIG. 11 is a side view of the internal components of the powered surgical instrument of FIG. 1 disposed in a second position, powered articulation.
Figure 13:
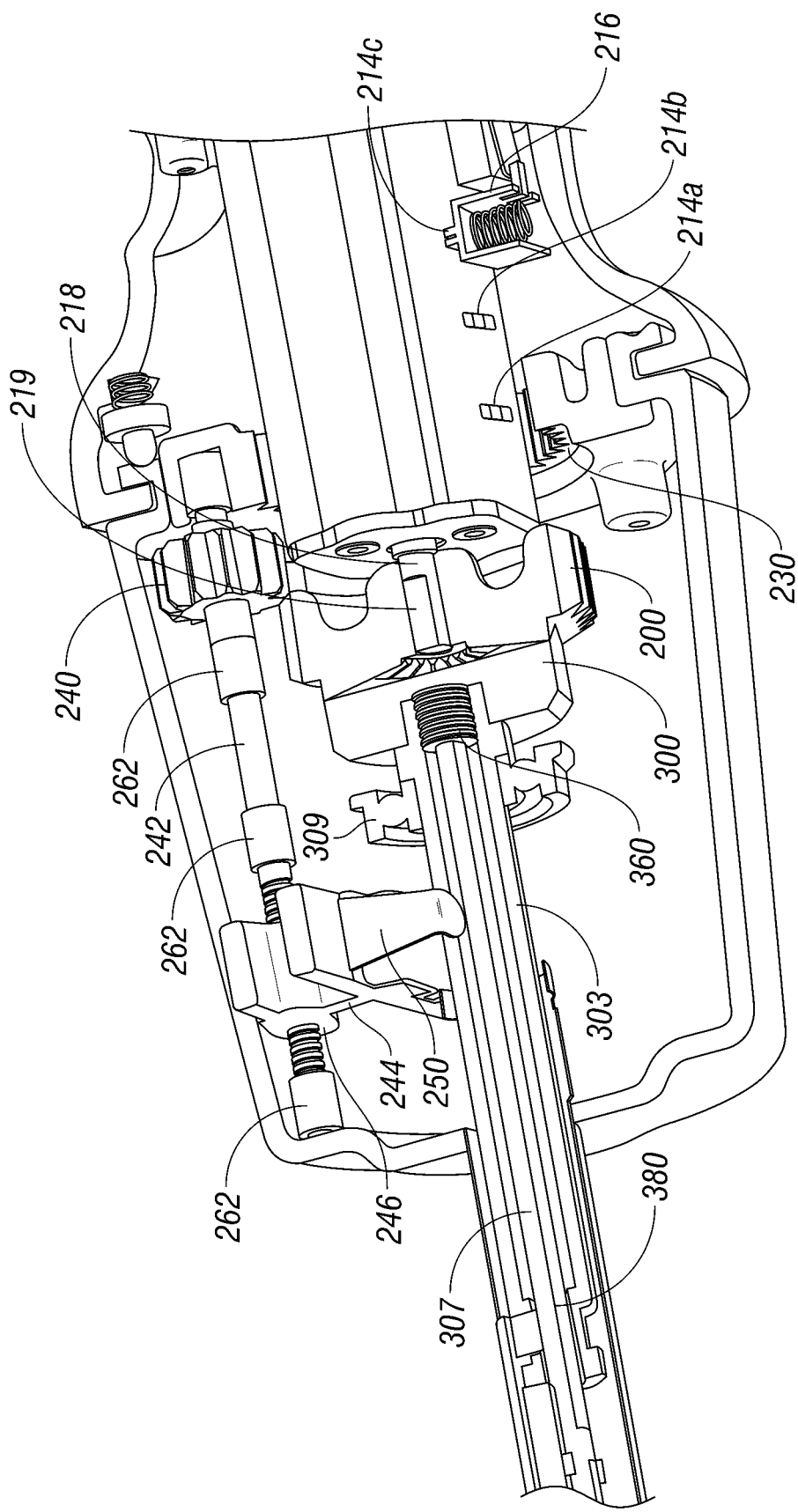
FIGS. 13-14 are perspective view of the internal components of the powered surgical instrument of FIG. 1 disposed in a third position, fire, clamp, grasp, retraction.
Figure 14:
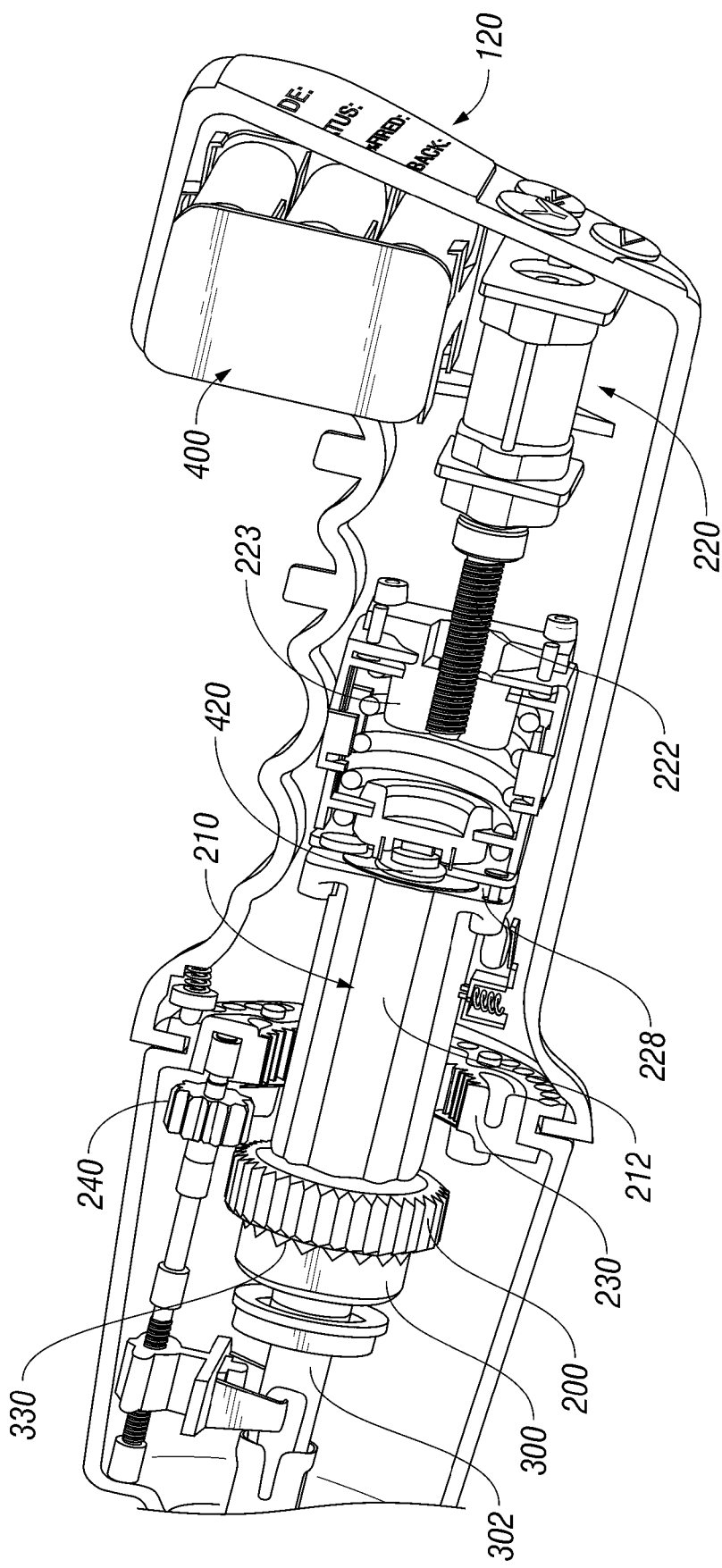

A cut away of the drive motor casing 212, at least partially surrounding drive motor 210, is illustrated in FIGS. 8-11. Drive motor casing 212 includes slots 214a, 214b and 214c therein. Each slot 214 is configured to mate with a position lock 216 to maintain drive gear 210 in a desired position. In FIG. 9, position lock 216 is shown mated with slot 214a—corresponding to drive gear 200 being in its first position. In FIG. 11, position lock 216 is shown mated with slot 214b—corresponding to drive gear 200 being in its second position. FIGS. 13 and 14 illustrate position lock 216 mated with slot 214c—corresponding to drive gear 200 being in its third position. Position lock 216, in the illustrated embodiments, is spring-loaded and biased against the drive motor casing 212, which maintains drive motor 210 is a desired position.

In the illustrated embodiments, shift motor 220 is located proximally of drive motor 210 and is configured to translate drive motor 210 along drive gear axis C-C between its first, second and third positions. Referring to FIG. 14, shift motor 220 is illustrated being driven by a shift screw 222 in conjunction with an internally-threaded screw housing 223, in accordance with a disclosed embodiment. It is further disclosed that a shift sensor 224 (See FIG. 8) (e.g., micro switch or optical/ferromagnetic proximity sensor activate by position lock 216), disposed adjacent position lock 216, electrically communicates with at least one switch 124 to start or stop shift motor 220 and/or provides feedback relating to the position of drive motor 210 (e.g., position of drive motor 210, such as "rotation," is displayed on screen 122 of user interface 120).

With reference to FIGS. 9 and 10, the first position of drive gear 200 is illustrated. Ring gear 230 is disposed within housing 110, wherein rotation of ring gear 230 causes rotation of endoscopic portion 140, end effector 160 and a distal housing portion 110a. Distal housing portion 110a is disposed distally of a proximal housing portion 110b. The housing portion 110a includes a guide channel 232 which is peripherally disposed therein and is configured to interface with a corresponding flange 234 which is peripherally disposed within the proximal housing portion 110b. In particular, the flange 234 is configured to slidably rotate within the guide channel 232 thereby allow for rotation of the housing portion 110a with respect to proximal housing portion 110b. In an embodiment, ring gear 230 is rigidly secured within distal housing portion 110a and is matingly engagable with drive gear 200. Thus, rotation of drive gear 200 causes rotation of the ring gear 230 and the housing portion 110a along with the end effector 160 about the longitudinal axis B-B.

In FIG. 6, a lip 235 is shown which isolates a user's hand from rotatable distal housing portion 110a. It is envisioned that a plurality of washers or ball-bearings (possibly made from synthetic resinous fluorine-containing polymers sold under the trademark TEFLON®) is disposed between distal housing portion 110a and proximal housing portion 110b to reduce the rotational friction therebetween.

With continued reference to the embodiment illustrated in FIG. 10, a plurality of detents 231 is disposed around a surface 233 of distal housing portion 110a. A tab 237 is shown disposed on proximal housing portion 110b. In a disclosed embodiment, tab 237 is distally biased (e.g., via tab spring 239) and in mechanical cooperation with at least one of plurality of detents 231. The combination of detents 231 and tab 237 helps secure distal housing portion 110a in a rotational position with respect to proximal housing portion 110b.

In FIG. 11, drive gear 200 is illustrated in its second position, as position lock 216 is aligned with slot 214b. Here, drive gear 200 is matingly engaged with an articulation gear 240, which is disposed at least partially within housing 110. Rotation of articulation gear 240 causes end effector 160 to move from its first position, where longitudinal axis B-B is substantially aligned with longitudinal axis A-A, towards its second position, wherein longitudinal axis B-B is disposed at an angle to longitudinal axis A-A.

In the illustrated embodiments and with specific reference to FIGS. 11 and 12, articulation of end effector 160 is affected by an articulation gear 240, an articulation screw 242, an articulation linkage 244 and at least one articulation rod 260. More specifically, articulation gear 240 is rigidly mounted to articulation screw 242, such that as articulation gear 240 is rotated by rotation of drive gear 200 while in its second position, articulation screw 242 also rotates. A plurality of bearings 262 is illustrated at various locations on articulation screw 242 to facilitate the retaining and aligning of articulation screw drive 242 as well as reducing the friction between articulation screw 242 and housing 110, for example.

With continued reference to FIG. 11, articulation screw 242 includes a threaded portion 246, which extends through an internally-threaded portion 248 of articulation linkage 244. This relationship between articulation screw 242 and articulation linkage 244 causes articulation linkage 244 to move distally and/or proximally (in the directions of arrows F and G) along threaded portion 246 of articulation screw 242 upon rotation of articulation screw 242. For example, as articulation screw 242 rotates in a first direction (e.g., clockwise), articulation linkage 244 move proximally, and as articulation screw 242 rotates in a second direction (e.g., counter-clockwise), articulation linkage 244 move distally.

At least one articulation arm 250 is shown extending from articulation linkage 244. In an embodiment, articulation arm 250 is rigidly connected to articulation rod 260 and it is envisioned that more than one articulation arm 250 is connectable to more than one articulation rod 260. As articulation linkage 244 is translated distally and/or proximally in response to rotation of articulation gear 240, articulation rod(s) 260 is also translated distally and/or proximally (in the directions of arrows F and G, along longitudinal axis A-A) in response thereto. Any combinations of limits switches, proximity sensors (e.g., optical and/or ferromagnetic), linear variable displacement transducers and shaft encoders (disposed within housing 110, for instance) may be utilized to control and/or record the location of articulation linkage 244 and/or articulation angle of end effector 160 and/or position of an actuation rod 306 as discussed below with reference to FIGS. 13 and 14.

Figure 12A:
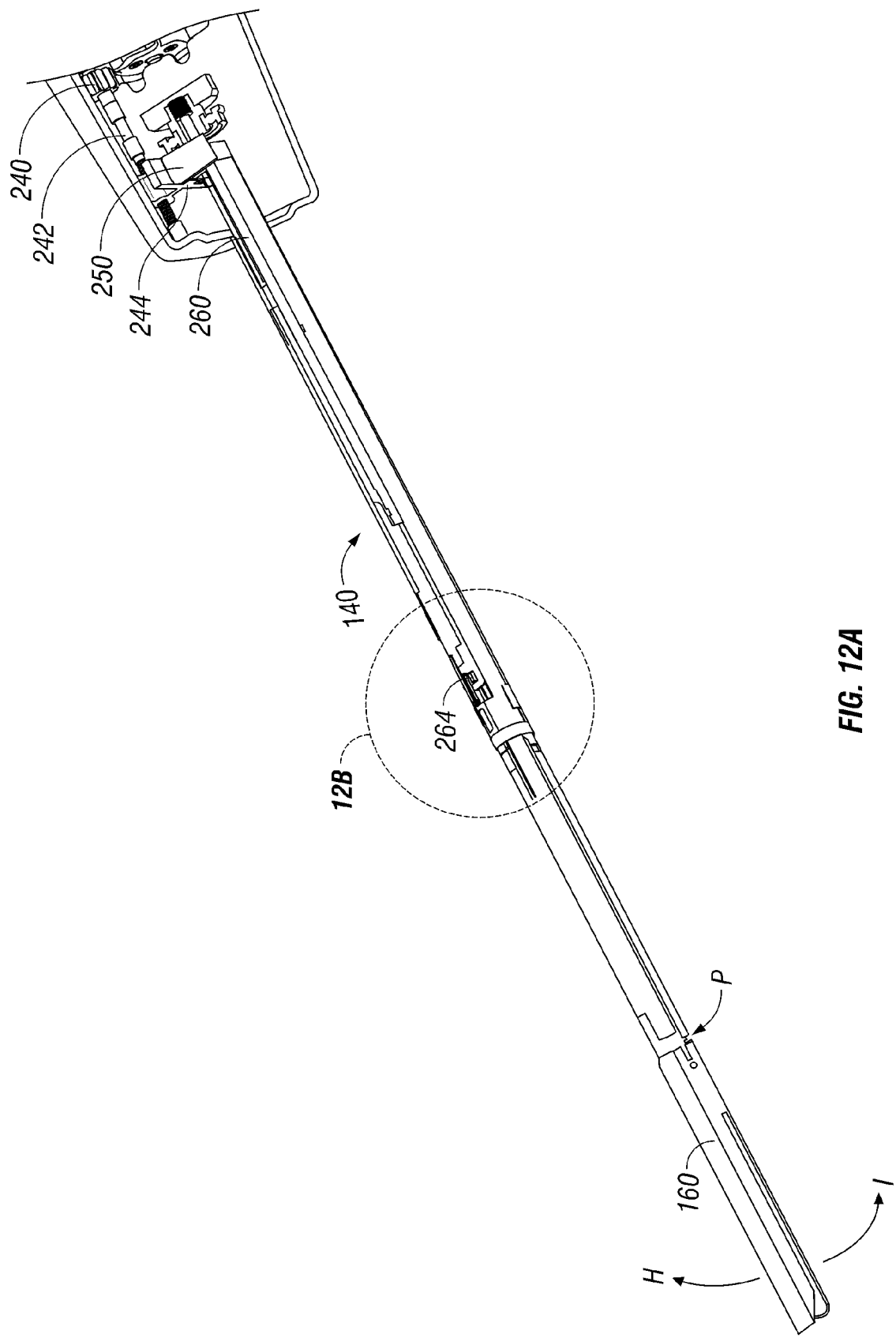
FIG. 12A is a perspective view including an endoscopic portion of the powered surgical instrument of FIG. 1 according to an embodiment of the present disclosure.
Figure 12B:
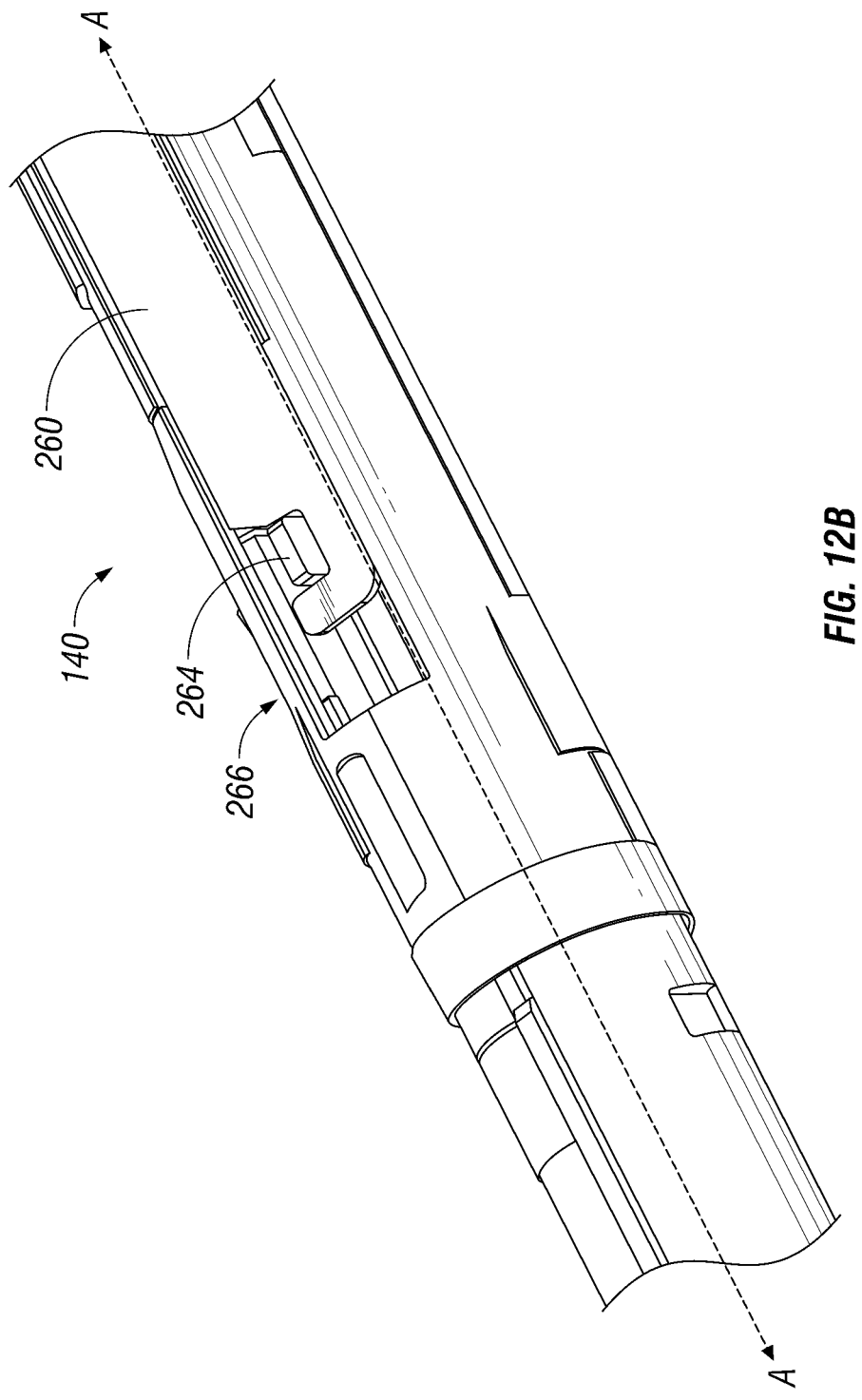
FIG. 12B is an enlarged perspective view of the portion of the powered surgical instrument indicated in FIG. 12A.

With reference to FIGS. 12A and 12B, articulation rod 260 is shown extending through at least a portion of endoscopic portion 140 and in mechanical cooperation with a linkage rod 264. Thus, linkage rod 264 similarly moves along longitudinal axis A-A upon rotation of articulation gear 240. A distal portion 266 of linkage rod 264 is in mechanical cooperation with end effector 160, such that proximal and distal movement of linkage rod 264 causes end effector 160 to move from its first position towards its second position about pivot P. More specifically, and for illustrative purposes, as linkage rod 264 moves distally, end effector 160 is articulated in the direction of arrow H and as linkage rod 264 is translated proximally, end effector 160 is articulated in the direction of arrow I. It is also envisioned that a portion of articulation rod 260 is in mechanical cooperation with end effector 160 to affect articulation thereof. Further details of providing articulation to end effector 160 are described in detail in commonly-owned U.S. Pat. No. 6,953,139 to Milliman et al., the contents of which are hereby incorporated by reference in their entirety.

With reference to FIGS. 13 and 14, drive gear 200 is illustrated in its third position, with position lock 216 aligned with slot 214c. The drive gear 200 is matingly engaged with an actuator gear 300, which is disposed at least partially within housing 110. More specifically, a set of teeth 202 disposed on a face 204 (FIG. 8) of drive gear 200 matingly engage actuator gear 300 to provide at least one of grasping tissue, clamping tissue, firing of end effector 160 (e.g., stapling and cutting) and retracting elements to their original position.

With reference to FIG. 13, a drive motor shaft 218 is shown extending from drive motor 210 and being connected to drive gear 220. A fastener (not explicitly shown in this embodiment) may be used to retain drive gear 220 on drive motor shaft 218. Drive motor shaft 218 is rotated by drive motor 210, thus resulting in rotation of drive gear 220. Drive motor shaft 218 is shown having a flat portion 219 (more than one flat portions 219 may be included), which allows "play" or "rotational float" between drive gear 220 and drive motor shaft 218 to facilitate tooth alignment and to help enable drive gear 220 to shift between positions. FIG. 13 also illustrates a bearing 309 disposed within housing 110 and at least partially surrounding drive tube 303. Bearing 309 facilitates rotation of drive tube 303 and aligns drive tube 303 through endoscopic portion 140.

In FIG. 14, a transducer 420 is shown adjacent drive motor 210 and shift motor 220. Transducer 420 (e.g., a force or pressure transducer) may measure and/or control the force required for the desired pressure on actuator gear 330. Transducer 420 may be in communication with portions of user interface 120, which may provide feedback to a user.

With reference to FIGS. 13 and 14, a drive tube 303 and an actuation rod 307 are also included. Drive tube 303 is rigidly attached to actuator gear 300. In an embodiment of the disclosure, actuation rod 307 extends at least to distal portion 142 of endoscopic portion 140 and is mechanically coupled to the firing rod 402. In response to rotation of drive gear 200, actuator gear 300 and drive tube 303 also rotate. As drive tube 303 rotates, the actuation rod 307 is driven forward by the threaded bung 360. Actuation rod 307 is prevented from rotation by flat/non-round features 380 which are mated to the tube housing cross section 266. When unlocked, rotation of actuation rod 307 rotates the firing rod 402 which closes the anvil assembly 302 of end effector 160 to grasp or clamp tissue held therebetween. Further details of firing end effector 160 (or actuation) are described in detail in commonly-owned U.S. Pat. No. 6,953,139 to Milliman et al., the entire contents of which are hereby incorporated by reference herein.

The firing rod 402 can be advanced distally to advance the actuation sled 330 either manually or automatically (e.g., via motorized mechanisms). An example of a powered stapler configured for advancing a firing rod to push fasteners through tissue is illustrated in a commonly-owned U.S. Patent Application entitled "Powered Surgical Stapling Device" by Marczyk, U.S. application Ser. No. 11/724,744, filed Mar. 15, 2007, the disclosure of which is hereby incorporated by reference herein in its entirety.

Figure 15A:
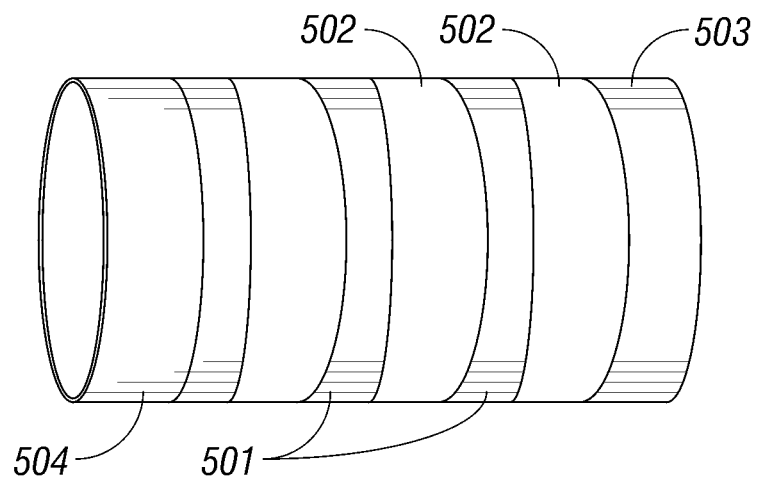
FIGS. 15A-B are perspective views of articulating shaft of the distal portion of the powered surgical instrument of FIG. 1.
Figure 15B:
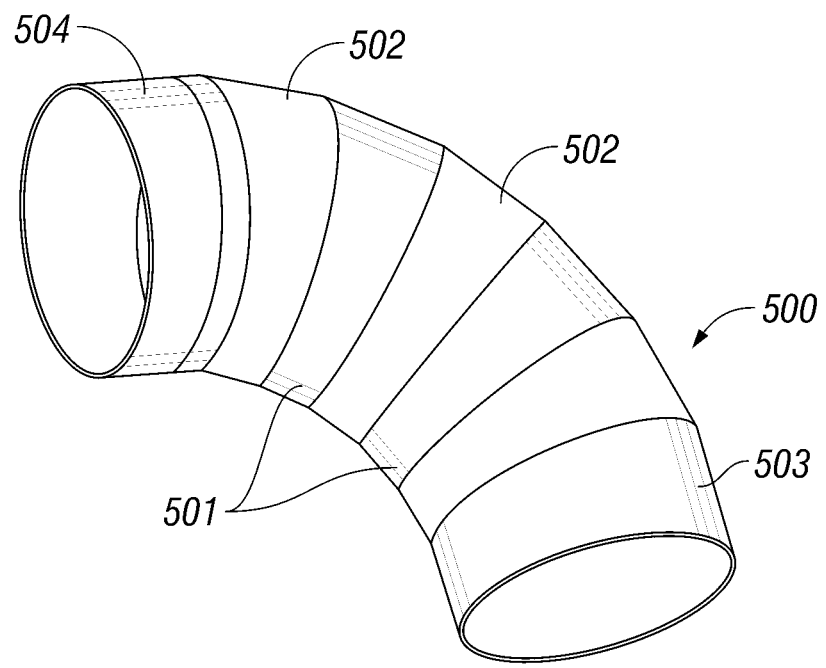

As discussed above, the firing rod 402 is disposed within the endoscopic portion 140 and the distal portion 142. Therefore, in embodiments where the firing rod 402 is formed from a flexible material it is desirable to provide flexible endoscopic portion 140 and distal portion 142. As shown in FIGS. 15A-B, the endoscopic and distal portions 140, 142 are shown as a flexible shaft 500. The flexible shaft 500 includes a plurality of interconnected angled outer tubes 501 and 502. FIG. 15A shows the flexible shaft in a non-articulated formation and FIG. 15B shows the flexible shaft 500 in full articulation formation. When the flexible shaft 500 is straight, narrow sections of the tubes 501 alternate with the wide sections of the tubes 502 as shown in FIG. 15A. When the flexible shaft 500 is fully articulated, the short sides and the wide sides of the tubes 501 and 502 are aligned as shown in FIG. 15B.

The flexible shaft 500 also includes a proximal drive end cap 503 which is in mechanical cooperation with the drive gear 200 and a distal end cap 504 which is in communication with another component of the surgical stapler 10 (e.g., the tool assembly 160 or the distal portion 142 depending where the flexible shaft 500 is disposed). The drive end cap 503 has only one angled face and is turned by the drive gear 200. The end cap 504 is fixed from rotation and also has one angled face and includes an internal stop member for mating with the neighboring tube.

The tubes 500 are mated together by a step which is disposed on the edges of inner surfaces of the tubes 500. The tubes 500 also include stop members at 180 degree positions which interface with neighboring tubes to turn against frictional forces. Each of the tubes 501 and 502 are angled by the same amount on corresponding mating faces and include alternative grooves and ribs which interlock the tubes 501 and 502.

Articulation is achieved by rotation of the tubes 501 and 502 either sequentially or independently. The drive end cap 503 is rotated continuously until the flexible shaft 500 has attained desired articulation position. As the drive end cap 503 is rotated, each tube is rotated correspondingly until the tube reached 90 degree rotation and then locks with the subsequent tube which then begins rotation of the subsequent tube, etc. Use of the flexible shaft 500 in manual or motor-driven instruments is contemplated. A designated motor, or a motor driving multiple functions of the instrument may be used. One of the positions of the shift motor 220 can engage a ring gear operatively connected to proximal drive end cap 503 so that drive gear 200 can drive rotation of the proximal drive end cap 503.

In further embodiments, the endoscopic portion 140 is configured to interchangeably mate with a variety of surgical end effectors including, but not limited to, circular surgical staplers, linear surgical staplers, and others. The endoscopic portion 140 may be relatively rigid, flexible (such as the shaft shown in FIGS. 15A and 15B) and/or articulating.

In certain embodiments, a digital control module (DCM) is desirably included in the housing 110 and can be configured and arranged to control or help control the operation of shift motor 220 and/or drive motor 210 to respond to the monitored information. Pulse modulation, which may include an electronic clutch, may be used in controlling the output. For example, the DCM can regulate the voltage or pulse modulate the voltage to adjust the power and/or torque output to prevent system damage or optimize energy usage. An electric braking circuit may be used for controlling the drive motor 210 and/or shift motor 220, which uses the existing back electromotive force (EMF) of rotating drive motor 210 to counteract and substantially reduce the momentum of drive gear 200. The electric braking circuit may improve the control of drive motor 210 and/or shift motor 220 for stopping accuracy and/or shift location of powered surgical instrument 100. Sensors for monitoring components of powered surgical instrument 100 and to help prevent overloading of powered surgical instrument 100 may include thermal-type sensors, such as thermal sensors, thermistors, thermopiles, thermo-couples and/or thermal infrared imaging and provide feedback to the DCM. The DCM may control the components of powered surgical instrument 100 in the event that limits are reached or approached and such control can include cutting off the power from the battery pack 400, temporarily interrupting the power or going into a pause mode, pulse modulation to limit the energy used, and the DCM can monitor the temperature of components to determine when operation can be resumed. The above uses of the DCM may be used independently of or factored with current, voltage, temperature and/or impedance measurements.

An identification system may also be included to determine and communicate to the DCM various information, including the speed, power, torque, clamping, travel length and strength limitations for operating the particular end effector 160. The DCM may also determine the operational mode and adjust the voltage, clutch spring loading and stop points for travel of the components. More specifically, the identification system may include a component (e.g., a microchip, emitter or transmitter) in end effector 160 that communicates (e.g., wirelessly, via infrared signals, etc.) with the DCM, or a receiver therein. It is also envisioned that a signal may be sent via firing rod, such that the firing rod functions as a conduit for communications between the DCM and end effector 160. The identification system communicates with the DCM information concerning the surgical instrument, such as, for example, the type of end effector attached to the surgical instrument and/or the status of the end effector.

In a disclosed embodiment, at least some of the information monitored by the various sensors in powered surgical instrument 100 may be provided to a video screen or monitoring system in an operating room. For instance, the data may be transmitted to a receiver for the operating room monitoring system from a communication transmitter incorporated in or associated with powered surgical instrument 100, via technology including Blue Tooth, ANT3, KNX, Z Wave, X10, wireless USB, WiFi, IrDa, Nanonet, Tiny OS, ZigBee, radio, UHF and VHF. Such features may facilitate monitoring by the user of powered surgical instrument 100 or other operating room or hospital personnel or remotely located persons.

It will be understood that various modifications may be made to the embodiments disclosed herein. For example, a shorter elongated tubular portion containing more or less coil fasteners may be provided for greater ease of handling during open surgery. Various articulations may be provided along the length of the elongated tubular portion to facilitate positioning of the coil fastener applier within the body. Additionally various configurations of the drive rod and slots or fastener retaining structure may be provided to accommodate various types of rotary fasteners. Therefore, the above description should not be construed as limiting, but merely as exemplifications of various embodiments. Those skilled in the art will envision other modifications within the scope and spirit of the claims appended hereto.

What is claimed is:

1. A surgical instrument, comprising:
   a housing having at least a drive motor, a shift motor, and a single drive gear in mechanical cooperation thereof;
   a shaft having a proximal end and a distal end, the proximal end of the shaft connected to the housing, the shaft defining a longitudinal axis therethrough; and
   an end effector connected to the distal end of the shaft;
   wherein the drive motor mechanically cooperates with the shift motor to actuate the single drive gear.

2. The surgical instrument of claim 1, wherein the drive motor enables rotation of the drive gear.

3. The surgical instrument of claim 1, wherein the shift motor enables the drive gear to move in a plurality of positions.

4. The surgical instrument of claim 1, wherein the drive motor, the shift motor, and the single drive gear are disposed along the longitudinal axis defined by the shaft.

5. The surgical instrument of claim 1, wherein the drive motor is placed adjacent the drive gear.

6. The surgical instrument of claim 1, wherein the drive motor is separated from the shift motor by a two-part housing, each part slidably engaged with the other.

7. The surgical instrument of claim 6, wherein one part is secured to a drive motor casing of the drive motor, whereas the other part is secured to the drive motor and is translatable within the housing of the surgical instrument.

8. The surgical instrument of claim 7, wherein the drive motor casing includes two slots, each slot configured to mate with a position lock to maintain the drive gear in one of a plurality of positions.

9. The surgical instrument of claim 8, wherein the position lock is spring-loaded and biased against the drive motor casing.

10. The surgical instrument of claim 9, wherein a shift sensor is disposed adjacent the position lock to electrically communicate with at least one switch to activate the shift motor and provide feedback relating to a position of the drive motor.

11. A surgical instrument, comprising:
    a housing having at least a drive motor, a shift motor, and a single drive gear in mechanical cooperation thereof;
    a shaft extending distally from the housing, the shaft defining a longitudinal axis therethrough, and the shaft having at least a first flexible segment and a second flexible segment, each segment being rotatably movable with respect to the other between a plurality of positions via a drive end cap in mechanical cooperation with the single drive gear, the drive end cap rotated continuously until each segment attains an articulated position; and
    an end effector disposed at a distal end of the shaft;
    wherein the drive motor mechanically cooperates with the shift motor to actuate the single drive gear.

12. The surgical instrument of claim 11, wherein the drive motor enables rotation of the drive gear.

13. The surgical instrument of claim 11, wherein the shift motor enables the drive gear to move in a plurality of positions.

14. The surgical instrument of claim 11, wherein the drive motor, the shift motor, and the single drive gear are disposed along the longitudinal axis defined by the shaft.

15. The surgical instrument of claim 11, wherein the drive motor is placed adjacent the drive gear.

16. The surgical instrument of claim 11, wherein the drive motor is separated from the shift motor by a two-part housing, each part slidably engaged with the other.

17. The surgical instrument of claim 16, wherein one part is secured to a drive motor casing of the drive motor, whereas the other part is secured to the drive motor and is translatable within the housing of the surgical instrument.

18. The surgical instrument of claim 17, wherein the drive motor casing includes two slots, each slot configured to mate with a position lock to maintain the drive gear in one of a plurality of positions.

19. The surgical instrument of claim 18, wherein the position lock is spring-loaded and biased against the drive motor casing.

20. The surgical instrument of claim 19, wherein a shift sensor is disposed adjacent the position lock to electrically communicate with at least one switch to activate the shift motor and provide feedback relating to a position of the drive motor.

* * * * *